United States Patent
Maehana et al.

(10) Patent No.: US 10,545,146 B2
(45) Date of Patent: Jan. 28, 2020

(54) METHOD FOR DETECTING SPECIFIC SUBSTANCE IN MILK

(71) Applicant: ASAHI KASEI KABUSHIKI KAISHA, Osaka-shi, Osaka (JP)

(72) Inventors: Koji Maehana, Tokyo (JP); Kenji Matsuyama, Tokyo (JP)

(73) Assignee: ASAHI KASEI KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 16/028,951

(22) Filed: Jul. 6, 2018

(65) Prior Publication Data

US 2018/0321239 A1 Nov. 8, 2018

Related U.S. Application Data

(62) Division of application No. 14/406,557, filed as application No. PCT/JP2012/065150 on Jun. 13, 2012, now Pat. No. 10,048,262.

(51) Int. Cl.
*G01N 33/569* (2006.01)
*B01D 61/14* (2006.01)
(Continued)

(52) U.S. Cl.
CPC ..... *G01N 33/56938* (2013.01); *B01D 61/142* (2013.01); *B01D 61/147* (2013.01);
(Continued)

(58) Field of Classification Search
None
See application file for complete search history.

(56) References Cited

U.S. PATENT DOCUMENTS 5,837,546 A 11/1998 Allen et al.
6,143,247 A 11/2000 Sheppard, Jr. et al.
(Continued)

FOREIGN PATENT DOCUMENTS

EP 0 323 605 A2 7/1989
JP 63-167799 A 7/1988
(Continued)

OTHER PUBLICATIONS

English translation of International Preliminary Report on Patentability and Written Opinion dated Dec. 24, 2014, in PCT International Application No. PCT/JP2012/065150.
(Continued)

*Primary Examiner* — Erik B Crawford
(74) *Attorney, Agent, or Firm* — Birch, Stewart, Kolasch & Birch, LLP

(57) ABSTRACT

An immunochromatographic method for detecting a specific substance contained in milk, which comprises (1) the step of contacting the milk with a test strip having a first part retaining a labeled first antibody directed to the specific substance or the specific substance that is labeled, a second part disposed downstream from the first part, on which a second antibody directed to the specific substance is immobilized, and a third part disposed upstream from the first part or the second part and having voids enabling removal of milk fat globules contained in the milk, at the third part or a further upstream part, and (2) the step of flowing the milk up to the second part or a further downstream part to obtain a detectable signal of the label at the second part or a further downstream part.

5 Claims, 3 Drawing Sheets

(51) Int. Cl.
  *G01N 33/558* (2006.01)
  *G01N 33/543* (2006.01)

(52) U.S. Cl.
  CPC ..... *G01N 33/54393* (2013.01); *G01N 33/558* (2013.01); *G01N 33/56911* (2013.01); *B01L 2300/0825* (2013.01); *G01N 2333/31* (2013.01); *G01N 2333/952* (2013.01)

(56) References Cited

U.S. PATENT DOCUMENTS

| | | |
|---|---|---|
| 6,197,598 B1 | 3/2001 | Schrier et al. |
| 6,268,478 B1 | 7/2001 | Adams |
| 2003/0032196 A1 | 2/2003 | Zhou |
| 2003/0036109 A1 | 2/2003 | Yazdankhah et al. |
| 2003/0073073 A1 | 4/2003 | Wolde-Mariam |
| 2004/0096356 A1 | 5/2004 | Degelaen et al. |
| 2005/0153370 A1 | 7/2005 | Lakshmi et al. |
| 2005/0196875 A1 | 9/2005 | Blatt et al. |
| 2005/0260695 A1 | 11/2005 | Fleming et al. |
| 2006/0127886 A1 | 6/2006 | Kaylor et al. |
| 2007/0192878 A1 | 8/2007 | Perreault |
| 2008/0194013 A1 | 8/2008 | Shida et al. |
| 2009/0087913 A1 | 4/2009 | Sakuma |
| 2010/0210022 A1 | 8/2010 | Madura |
| 2012/0003662 A1 | 1/2012 | Madura |

FOREIGN PATENT DOCUMENTS

| | | |
|---|---|---|
| JP | 1-244370 A | 9/1989 |
| JP | 11-028099 | 2/1999 |
| JP | 11-28099 A | 2/1999 |
| JP | 11-505327 A | 5/1999 |
| JP | 2002-214236 A | 7/2002 |
| JP | 2003-512624 A | 4/2003 |
| JP | 2007-060970 A | 3/2007 |
| JP | 2008-524582 A | 7/2008 |
| JP | 2010-008361 A | 1/2010 |
| WO | WO 93/02098 | 2/1993 |
| WO | WO 99/34191 | 7/1999 |
| WO | WO 01/29558 A1 | 4/2001 |
| WO | WO 01/81915 A1 | 11/2001 |
| WO | WO 02/075310 A1 | 9/2002 |
| WO | WO 2005/121794 A1 | 12/2005 |
| WO | WO 2008/037026 A1 | 4/2008 |
| WO | WO 2011/087789 A2 | 7/2011 |
| WO | WO 2011/113160 A1 | 9/2011 |

OTHER PUBLICATIONS

JRA Advanced Livestock Management System Utilization Report (Heisei 18 to 20 fiscal years (2006-2008)) pp. 58-65.

Kim et al., "Optimization of the PCR for Detection of *Staphylococcus aureus* nuc Gene in Bovine Milk," J. Dairy Sci (2001), vol. 84, pp. 74-83.

Extended European Search Report issued in European Patent Application No. 12878885.8 dated Jun. 17, 2016.

Partial Supplementary European Search Report for European Application No. 12878885.8, dated Mar. 17, 2016.

Schalkhammer, "Analytical Biotechnology," Jan. 1, 2002, p. 157 (3 pages total), XP055220116.

Yazdankhah et al., "Rapid and Sensitive Detection of *Staphylococcus* Species in Milk by ELISA based on Monodisperse Magnetic Particles", Veterinary Microbiology, vol. 62 (1998) pp. 17-26.

[Fig.1]
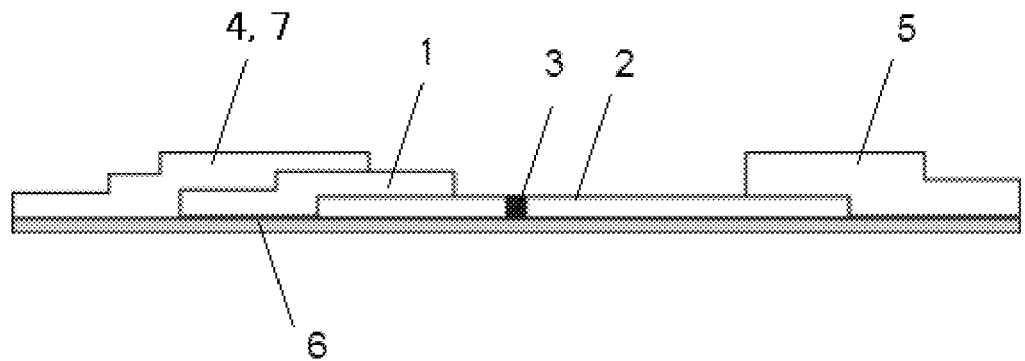
[Fig.2]
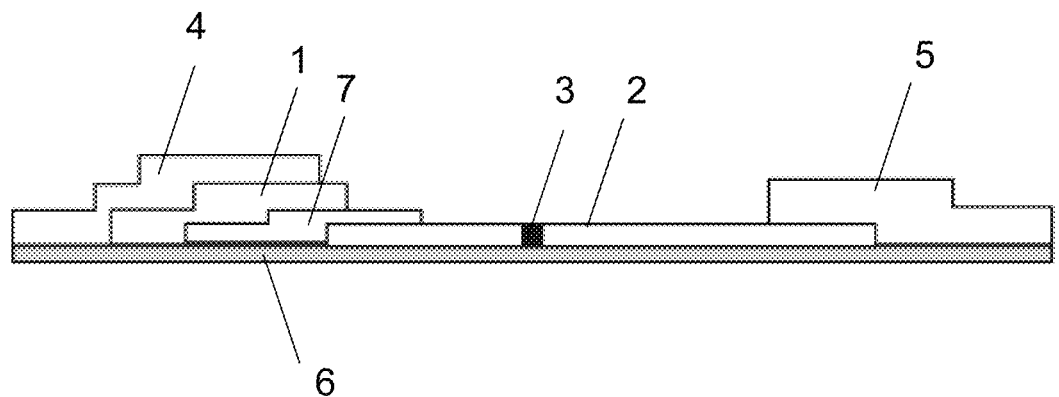
[Fig.3]
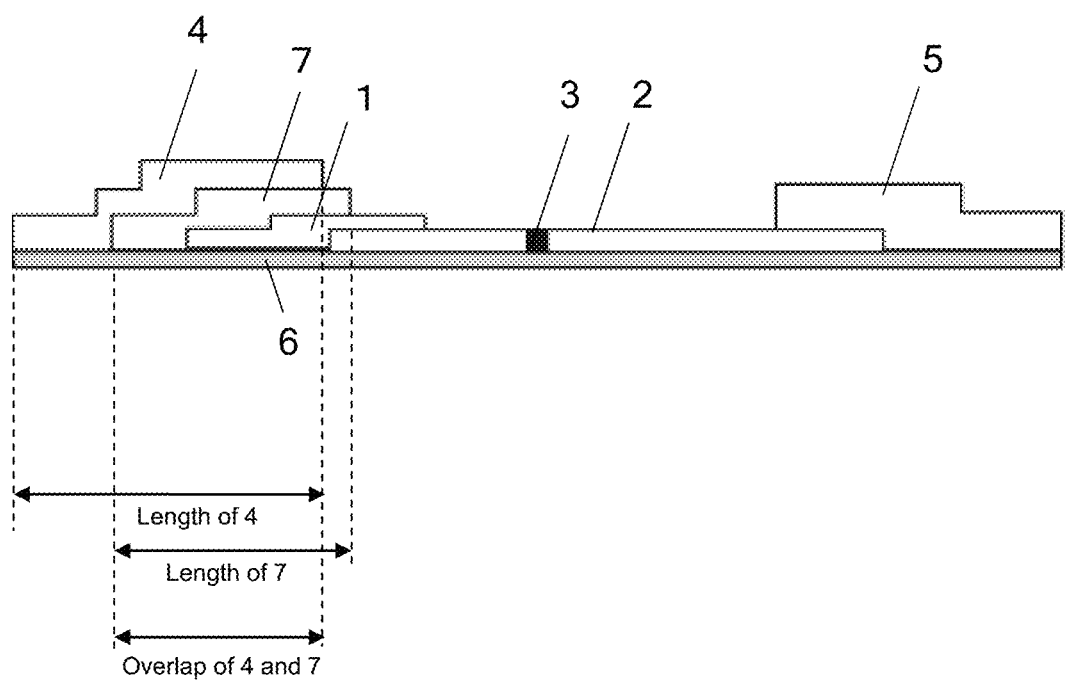

[Fig.4]
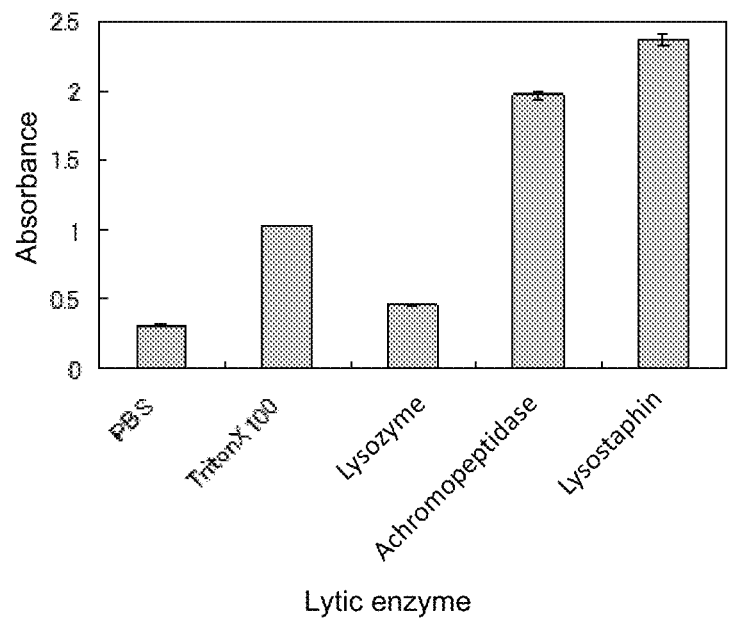
[Fig.5]
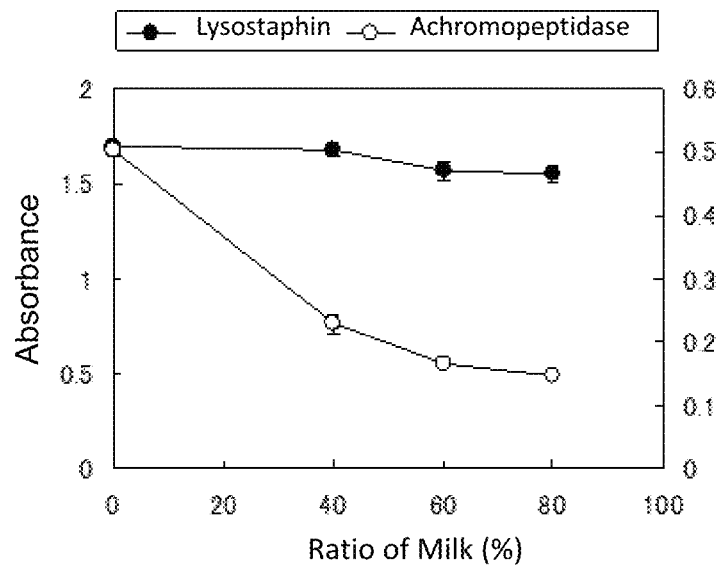

[Fig.6]
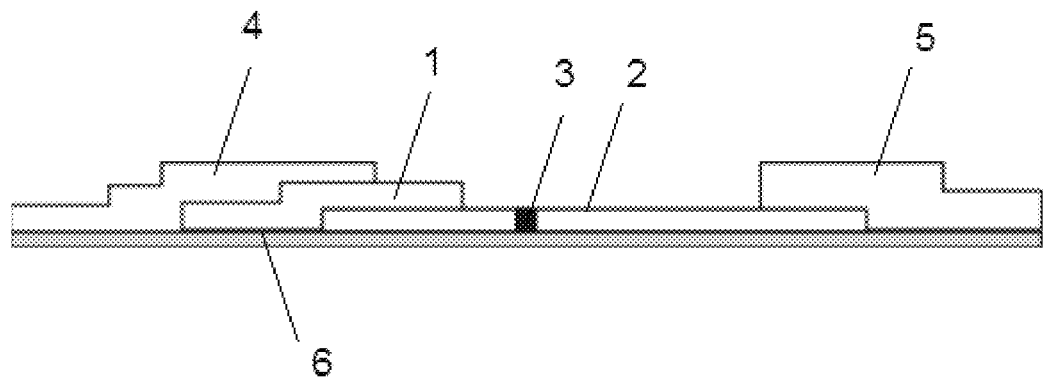
[Fig.7]
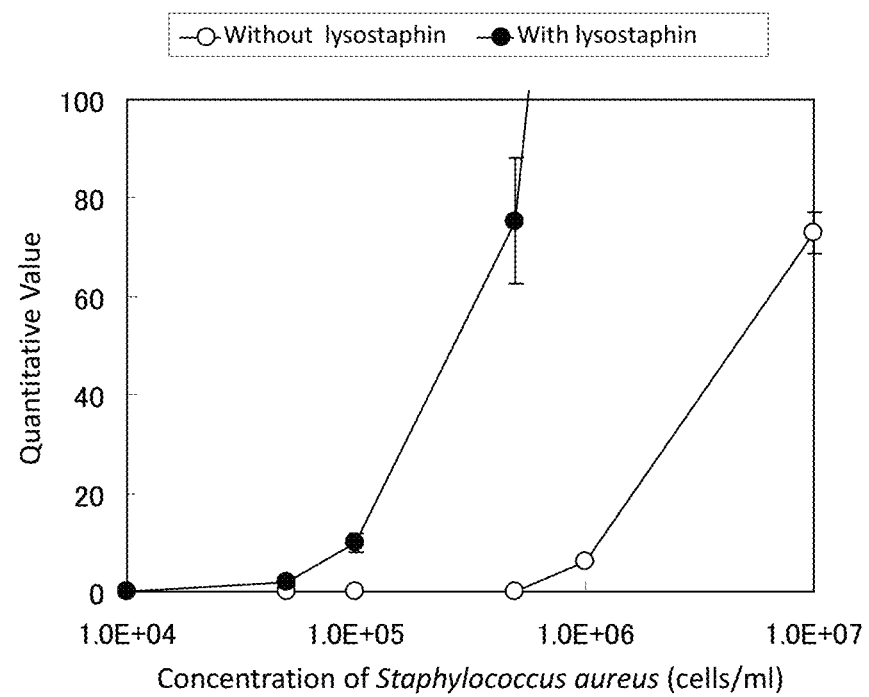

METHOD FOR DETECTING SPECIFIC SUBSTANCE IN MILK

CROSS-REFERENCE TO RELATED APPLICATION

This application is a Divisional of copending application Ser. No. 14/406,557, filed on Dec. 9, 2014, which is the National Phase under 35 U.S.C. § 371 of International Application No. PCT/JP2012/065150, filed on Jun. 13, 2012, all of which are hereby expressly incorporated by reference into the present application.

TECHNICAL FIELD

The present invention relates to an immunochromatographic method and immunochromatographic device for detecting a substance in milk by using an antigen-antibody reaction.

BACKGROUND ART

Milk of livestock animals, of which typical examples are cow, sheep, and goat, is not sterile, and may be contaminated with certain microorganisms due to diseases or environment. In particular, it is known that animals with a disease caused by infection of a microorganism often discharge a lot of the microorganisms into milk. Typical diseases of livestock animals caused by infection of a microorganism include mastitis.

Mastitis is inflammation of the laticifer system or milk gland tissue, and it is caused largely by invasion, ecesis, and proliferation of a microorganism in the udder. Although many kinds of animals contract mastitis, it is said that, especially concerning cow's mastitis in dairy cows, 15 to 40% of the whole dairy cows contract mastitis, and thus it is one of the extremely important diseases for dairy farmers. If a dairy cow contracts mastitis, not only the milk synthesis function is inhibited to result in reduction of lactation amount, or even stop of lactation as the case may be, but also enormous economical losses such as cost of medical treatment and penalty concerning milk price are imposed on dairy farmers. Furthermore, it also increases the labor of dairy farmers, since, for example, milking of teats suffering from mastitis must be separately performed for preventing infection.

Mastitis is caused by infection of various microorganisms, but antibiotics that exhibits efficacy against mastitis may differ depending on type of causative microorganism, and certain types of microorganisms have different characteristics concerning, for example, transmission to other teats or individuals, or post-infectious handling thereof differs. Therefore, it is extremely important to quickly and conveniently identify the causative microorganism existing in milk.

As methods for identifying a causative microorganism of an infectious disease, there are known cultivation-based identification method, gene-based identification method, and antigen-antibody reaction-based identification method. Although the current mainstream of the method for identifying a causative microorganism of mastitis of livestock animals is the cultivation-based identification method, the operation thereof is complicated, and in addition, it has a problem of requiring several days for obtaining results. There has also been reported an identification method based on detection of a specific gene by a gene amplification method (PCR method) (Non-patent document 1). Although results can be obtained in about one day by this method, it still has a problem of requiring special instruments and maneuvers. In recent years, there has been developed an apparatus for detecting *Staphylococcus aureus*, which is one of the causative microorganisms of mastitis, or *Escherichia coli* by surface plasmon resonance (SPR) on the basis of an antigen-antibody reaction (Non-patent document 2). For this apparatus, an antibody against an antigen specific to each bacterium is prepared, and this antibody is fixed on an SPR chip and used. Although this method enables quick detection of a specific causative microorganism, it requires a special apparatus, and therefore it is difficult to perform measurement by this method on practical dairy spots etc.

Simple measurement devices which enable quick and convenient measurement in the home or clinic for biosamples such as blood and urine utilizing immunochromatography (immunochromatographic device) have widely been used (for example, refer to Patent document 1). The method performed in such devices uses a test strip comprising test paper containing a first antibody specific to a target substance of measurement (antigen) and labeled with coloring particles such as gold colloid, and a porous membrane on which a second antibody for capturing the target substance of measurement is immobilized, which test paper and porous membrane are linked together. If a test sample containing a target substance of measurement is dropped onto the strip, the target substance of measurement binds with the antibody labeled with coloring particles and/or the antibody immobilized on the porous membrane, resulting a visually distinguishable line or the like on the membrane. Therefore, by confirming presence or absence of such a line or the like, presence or absence of the substance to be measured can be detected.

Although Patent document 1 teaches that the aforementioned method can be applied to, besides blood (whole blood), plasma, serum, urine, saliva, sputum, sweat, and so forth, it does not teach application of the aforementioned method to milk of livestock animals, and does not teach nor suggest the problems encountered at the time of such application at all. Further, although methods for applying an immunochromatographic method to biosamples such as blood (whole blood) as a test sample are also disclosed in Patent documents 2 to 4, these patent documents do not teach nor suggest application of immunochromatographic method to milk of livestock animals, either.

For a simple measurement device that enables quick and convenient measurement for milk of livestock animals as a test sample by using an immunochromatographic method at practical dairy spots, Patent document 5 proposes a method of using the immunochromatographic method for milk as a test sample for the purpose of inspecting causative microorganisms of mastitis of livestock animals. This patent document teaches that milk fat globules and casein contained in milk inhibit detection by the immunochromatographic method, and it is preferred that they are removed in advance before the test. Although this patent document discloses a method of removing milk fat globules and casein by leaving milk standing, separating a cream layer, and performing a treatment with a surfactant, it does not teach removal of milk fat globules with a filter.

Further, although Patent documents 2 to 4 teach techniques of removing contaminants with a physical filter or a membrane showing chemical affinity for use in applying immunochromatographic method, the methods described in these references are methods of applying the immunochromatographic method to biosamples such as whole blood as described above, and they are not methods of applying it to milk of livestock animals. Patent documents 1 to 4 do not teach nor suggest the problems encountered at the time of applying the immunochromatographic method to milk of livestock animals, and do not teach any means for solving the problems at all.

PRIOR ART REFERENCES

Patent Documents

Patent document 1: Japanese Patent Unexamined Publication (KOKAI) No. 1-244370
Patent document 2: Japanese Patent Unexamined Publication (KOHYO) No. 2003-512624
Patent document 3: Japanese Patent Unexamined Publication (KOHYO) No. 11-505327
Patent document 4: Japanese Patent Unexamined Publication (KOKAI) No. 2002-214236
Patent document 5: International Patent Publication WO02/075310

Non-Patent Documents

Non-patent document 1: J. Dairy. Sci., 84:74-83
Non-patent document 2: JRA Advanced Livestock Management System Utilization Report (Heisei 18 to 20 fiscal years), pp. 58-65

SUMMARY OF THE INVENTION

Object to be Achieved by the Invention

An object to be achieved by the present invention is to provide an immunochromatographic method and immunochromatographic device for detecting a substance in milk of a livestock animal using an antigen-antibody reaction.

Means for Achieving the Object

The inventor of the present invention examined identification of causative microorganisms of mastitis on the basis of an antigen-antibody reaction using an immunochromatographic device. However, when the inventor of the present invention examined whether a microorganism could actually be detected by the immunochromatographic method using milk as a sample, it was found that the antigen-antibody reaction did not advance on a test strip of the immunochromatographic device. The inventor of the present invention investigated the cause of the no smooth advance of antigen-antibody reaction on the test strip, and as a result, considered that the cause of the above phenomenon might be clogging of the test strip linked with a porous membrane in the immunochromatographic device with a lot of milk fat globules contained in milk, resulting in insufficient flow of a developing solution. Immunochromatographic devices usually use a test strip having a pore diameter of several tens to several hundreds nm for transportation by the developing solution, and in order to obtain appropriate rate of the antigen-antibody reaction. Milk immediately after milking contains a lot of milk fat globules having a diameter of around 1 to ten and several micrometers (although the particle diameter of milk fat globules in marketed milk or the like is made to be 1 μm or smaller by a homogenization treatment of the milk fat globules in fresh milk, milk not subjected to the homogenization treatment contains milk fat globules having a wide range of particle sizes), and it was considered that the particle size distribution of the milk fat globules was extremely larger than that of erythrocytes, and therefore they causes clogging of the membrane to make the measurement difficult.

The inventor of the present invention conducted various researches in order to achieve the aforementioned object, as a result, found that measurement of a specific substance contained in milk by the immunochromatographic method was enabled by trapping a part of milk fat globules contained in the milk by a sizing treatment on the upstream side of the test strip used in the immunochromatographic method, and accomplished the present invention.

Thus, the present invention is as follows.

[1] An immunochromatographic method for detecting a specific substance in milk, which comprises:
(1) the step of contacting the milk with a test strip having a first part retaining a labeled first antibody directed to the specific substance or retaining the specific substance that is labeled, a second part disposed downstream from the first part, on which a second antibody directed to the specific substance is immobilized, and a third part disposed upstream from the first part or the second part and having voids enabling removal of milk fat globules contained in the milk, at the third part or a further upstream part, and (2) the step of flowing the milk up to the second part or a further downstream part to obtain a detectable signal of the label at the second part or a further downstream part.

[2] The method according to [1], wherein the immunochromatographic method is a lateral flow type method.

[3] The method according to [1] or [2], wherein a labeled first antibody directed to the specific substance is retained at the first part.

[4] The method according to any one of [1] to [3], wherein the specific substance is a component of a bacterium, or a substance secreted by a bacterium.

[5] The method according to any one of [1] to [4], wherein at least one or both of the first antibody and the second antibody are monoclonal antibodies.

[6] The method according to [5], wherein the first antibody and the second antibody are monoclonal antibodies.

[7] The method according to any one of [1] to [6], wherein retention particle size of the voids of the third part is 1 to 3.5 μm.

[8] The method according to any one of [1] to [7], wherein the third part is constituted by two or more kinds of members having voids that can remove milk fat globules of different particle sizes.

[9] The method according to [8], wherein the third part is constituted by a first member disposed downstream and a second member disposed upstream, and retention particle size of the second member is larger than retention particle size of the first member.

[10] The method according to [9], wherein the retention particle size of the first member is 1.0 to 2.0 μm, and the retention particle size of the second member is 3.0 to 3.5 μm.

[11] The method according to any one of [1] to [10], which comprises the step of flowing milk subjected to a treatment with a lytic enzyme up to the second part or a further downstream part.

[12] The method according to [11], wherein the lytic enzyme is an autolysin.

[13] The method according to [11], wherein a *staphylococcus* contained in the milk is detected by using lysostaphin as the lytic enzyme.

[14] A method for diagnosing whether a causative microorganism of mastitis of a livestock animal is a *staphylococcus* or not, which comprises:
the step of obtaining milk containing the causative microorganism from the livestock animal suffering from mastitis, the step of mixing a lytic enzyme in the milk so that a specific substance existing in cells of the causative microorganism is released out of the cells, and the step of determining presence or absence of the specific substance or measuring existing amount of the specific substance by an immunological method using an antibody directed to the specific substance as an antigen.

[15] The method according to [14], wherein whether the causative microorganism is a *staphylococcus* or not is diagnosed by using lysostaphin as the lytic enzyme.

[16] An immunochromatographic device for detecting a specific substance contained in milk, which comprises a test strip having a first part retaining a labeled first antibody directed to the specific substance or retaining the specific substance that is labeled, a second part disposed downstream from the first part, on which a second antibody directed to the specific substance is immobilized, and a third part disposed upstream from the first part or the second part and having voids enabling removal of milk fat globules contained in the milk.

[17] The immunochromatographic device according to [16], wherein the first part or the second part retains a lytic enzyme or a surfactant.

[18] A detection kit consisting of an additive solution containing a lytic enzyme or a surfactant, and the immunochromatographic device according to [16].

Effect of the Invention

According to the present invention, presence or absence of a specific substance in milk can be quickly and conveniently detected on site. In particular, when it is desired to diagnose cow's mastitis, if a visually recognizable label is used, the detection can be carried out in dairy farms without using any apparatus etc., and a treatment for removing the cream layer is also unnecessary. Therefore, the causative microorganism can be quickly identified before further aggravation of the condition of the disease, and right treatment policies such as selection of appropriate antibiotics, and measure for preventing expansion of the infection can be determined at an early stage.

BRIEF DESCRIPTION OF THE DRAWINGS

FIG. 1 shows a schematic sectional view of the test strip of the immunochromatographic device used in Example 1, which comprises a labeled antibody-impregnated member 1 (first part), a membrane carrier 2 for chromatographic development (second part), a part 3 for capturing, a member 4 for sample addition, a member 5 for absorption, a substrate 6, and a member 7 for removal of fat globules (third part).

FIG. 2 shows a schematic sectional view of another example of the test strip of the immunochromatographic device.

FIG. 3 shows a schematic sectional view of further another example of the test strip of the immunochromatographic device.

FIG. 4 shows detection sensitivity-improving effect of use of an autolysin.

FIG. 5 shows the results of the measurement of *Staphylococcus aureus* added to cow's milk based on ELISA using achromopeptidase and lysostaphin.

FIG. 6 shows a schematic sectional view of the test strip of the immunochromatographic device used in Example 6, which comprises a labeled antibody-impregnated member 1 (first part), a membrane carrier 2 for chromatographic development (second part), a part 3 for capturing, a member 4 for sample addition, a member 6 for absorption, and a substrate 6.

FIG. 7 shows the results of detection of *Staphylococcus aureus* contained in milk by the immunochromatographic method using lysostaphin as a lytic enzyme.

MODES FOR CARRYING OUT THE INVENTION

Hereafter, the present invention will be explained in more detail.

The immunochromatographic device of the present invention is a device for detecting a specific substance contained in milk by the immunochromatographic method, which comprises a test strip having a first part retaining a labeled first antibody directed to the specific substance or the specific substance that is labeled, a second part disposed downstream from the first part, on which a second antibody directed to the specific substance is immobilized, and a third part disposed upstream from the first part or the second part and having voids enabling removal of milk fat globules in the milk. Specific examples of the structure of the test strip include those of the test strips of which schematic sectional views are shown in FIGS. 1, 2, and 3. In FIG. 1, the member 4 for sample addition and the member 7 for removal of fat globules (third part) are integrally disposed upstream from the labeled antibody-impregnated member (first part) 1. In FIG. 2, the member 7 for removal of fat globules (third part) is disposed downstream from the labeled antibody-impregnated member (first part) 1, and upstream from the membrane carrier 2 for chromatographic development (second part). In FIG. 3, the member 7 for removal of fat globules (third part) is disposed downstream from the member 4 for sample addition, and upstream from the labeled antibody-impregnated member (first part) 1.

The immunochromatographic device can be produced in a known manner by using marketed materials.

The material used for the first part is not particularly limited, so long as a material enabling immunochromatography is chosen, but preferred examples include a fiber matrix of cellulose derivative etc., filter paper, glass fiber, cloth, cotton, and so forth.

The material used for the second part is not particularly limited, so long as a material enabling immunochromatography is chosen, but preferred examples include cellulose nitrate, mixed cellulose nitrate ester, polyvinylidene fluoride, nylon, and so forth.

The material used for the third part preferably has voids that enable removal of milk fat globules contained in milk and having a diameter of about 1 to ten and several micrometers. The third part must be disposed upstream from the aforementioned second part consisting of a porous membrane having a pore diameter of several tens to several hundreds nm, and preferably disposed upstream from the aforementioned first part, i.e., at a position at which a sample solution first contacts with and passes through the test strip.

The voids of the third part may have a size that enables removal of milk fat globules, and retention particle size is preferably 0.1 to 10 μm, more preferably 1 to 3.5 μm. The material is not particularly limited, so long as a material having voids showing a retention particle size within the aforementioned range is chosen, but preferred examples include a matrix of fibers such as cellulose derivatives, filter paper, glass fiber, cloth, cotton, and so forth. The retention particle size means such a particle size of milk fat globules that milk fat globules having a particle size not smaller than the retention particle size cannot pass through the voids and retained by third part, and substantially corresponds to average pore size of the voids of the third part, and 50% or more, preferably 60% or more, more preferably 70% or more, still more preferably 80% or more, particularly preferably 90% or more, most preferably 98% or more, of milk fat globules having a particle size not smaller than the retention particle size cannot pass through the voids and retained by the third part. Ratio of milk fat globules to be retained can be measured by a method well known to those skilled in the art. For example, it is described that the retention particle size of GF/B provided by GE Healthcare Bioscience is 1.0 μm in the catalogue thereof (particle retention), and such a particle size as mentioned above can be confirmed by a method well known to those skilled in the art.

The aforementioned third part may consist of a single kind of material having a specific retention particle size, or may consist of a laminate comprising materials having different retention particle sizes and integrally adhered so that the retention particle size becomes smaller stepwise, in order to increase milk fat globule separation efficiency. Such a third part as mentioned above constituted by two or more kinds of members that can remove milk fat globules of different particle sizes constitutes a preferred embodiment of the present invention, and in a more preferred embodiment of the present invention, the third part is constituted with a first member disposed downstream and a second member disposed upstream, and the retention particle size of the second member is larger than the retention particle size of the first member. When the third part is constituted with such two kinds of members, it is preferred that the retention particle size of the first member disposed downstream is 1.0 to 2.0 μm, and the retention particle size of the second member disposed upstream is 3.0 to 3.5 μm. In order to detect a specific substance from milk containing milk fat globules of high concentration and wide particle size distribution, preferably such milk undiluted after milking, with high sensitivity, it is preferred that the third part is constituted with a combination of a member having a small retention particle size and a member having a large retention particle size.

The aforementioned first part retains a labeled first antibody directed to a specific substance, or a labeled specific substance. If the first part retains a labeled first antibody directed to a specific substance, the specific substance can be detected by the sandwich assay method. Further, if the first part retains a labeled specific substance, the specific substance can be detected by the competition method. Since the sandwich assay method shows high detection sensitivity and gives a line indicating detection of antibody as a positive result, it is more preferred for the present invention, and therefore the first part preferably retains a labeled first antibody directed to a specific substance.

When the first part is made to retain a labeled first antibody directed to a specific substance, two kinds of antibodies, the first antibody directed to the specific substance, and a second antibody directed to the specific substance. In order to enable detection of the specific substance by the sandwich assay method, the aforementioned first antibody and second antibody are antibodies that can simultaneously bind to the specific substance, and it is preferred that the epitope of the specific substance to be recognized by the aforementioned first antibody is different from the epitope of the specific substance to be recognized by the aforementioned second antibody.

In the present invention, in order to obtain a detectable signal, the first antibody or the specific substance retained by the first part is labeled. Examples of the label used for the present invention include a coloring particle, enzyme, radioisotope, and so forth, and it is preferable to use a coloring particle that can be visually detected without any special equipment. Examples of the coloring particle include metal microparticles such as those of gold and platinum, nonmetallic particles, latex particles, and so forth, but it is not limited to these. The coloring particle may have any size so long as the coloring particle have such a size that it can be transported downstream through the inside of the voids of the test strip, but it preferably has a size of 1 nm to 10 μm, more preferably 5 nm to 1 μm, still more preferably 10 to 100 nm, in diameter.

The specific substance measured by the present invention may be any substance so long as it is a substance that can be measured by the immunochromatographic method, but it is preferably a component of a bacterium or a substance that is secreted by a bacterium. The specific substance is more preferably the L7/L12 ribosomal protein of a bacterium. High detection sensitivity can be obtained for the L7/L12 ribosomal protein, since it exists in cells in a large copy number. Further, as shown in the examples mentioned later, an antibody with which a specific bacterium as a cause of mastitis can be distinguished from other bacteria at a species or genus level can be actually obtained by a known method. Type of the bacterium is not particularly limited, and it may be a gram-positive bacterium, or a gram-negative bacterium. Examples include, for example, gram-positive bacteria such as staphylococci (bacteria belonging to the genus *Staphylococcus*), preferably *Staphylococcus aureus*, and so forth, *Escherichia coli*, bacteria belonging to the genus *Klebsiella*, and so forth, but it is not limited to these.

The aforementioned antibody can be prepared by the method described in International Patent Publication WO00/06603. When the bacterial ribosomal protein L7/L12 is the antigen, the antibody can be prepared by using a full length protein or a partial peptide of the bacterial ribosomal protein L7/L12 as an antigen, but it is preferably prepared by using a full length protein as an antigen. An antiserum containing an antibody (polyclonal antibody) that recognizes the L7/L12 ribosomal protein can be obtained by inoculating such a partial peptide or full length protein as mentioned above as it is or crosslinked with a carrier protein to an animal, together with an adjuvant as required, and collecting the serum of the animal. Further, the antibody can also be purified from the antiserum, and used. Examples of the animal used for the inoculation include sheep, horse, goat, rabbit, mouse, rat, and so forth, and sheep, rabbit, and so forth are especially preferred for preparing polyclonal antibodies. Further, it is more preferable to use, as the antibody, a monoclonal antibody obtained by a known method in which a hybridoma cell is prepared, and in such a case, mouse is preferred as the animal. As such a monoclonal antibody, if a monoclonal antibody that reacts with the ribosomal protein L7/L12 of a specific bacterium that causes mastitis, but does not react with the ribosomal protein L7/L12 of a bacterium that causes mastitis other than the above specific bacterium is retrieved by screening, it can be utilized for diagnosing whether an animal suffers from infection by the bacterium or not.

An antibody that recognizes a substance other than the ribosomal protein L7/L12 as an antigen may also be used, so long as the antibody is a monoclonal antibody that reacts with a component of a specific bacterium that causes mastitis or a substance secreted by such a bacterium, but does not react with a component of a bacterium that causes mastitis other than the foregoing bacterium or a substance secreted by such a bacterium.

Further, as the monoclonal antibody, it is preferable to use a monoclonal antibody of which antigen-antibody reaction is not inhibited with any contaminants other than the specific substance contained in milk. For example, milk contains a large amount of proteins such as casein, and they may inhibit the reaction of the specific substance and the monoclonal antibody. As the monoclonal antibody directed to the specific substance prepared in a conventional manner, for example, a monoclonal antibody of which antigen-antibody reaction is not inhibited by casein or the like, or a monoclonal antibody of which antigen-antibody reaction is hardly affected by casein or the like may be preferably chosen and used. Such a monoclonal antibody can be easily prepared by preparing monoclonal antibodies that specifically react with an antigen in a usual manner, and then selecting a monoclonal antibody of which antigen-antibody reaction is not substantially inhibited by a contaminant such as casein by examining whether the antigen-antibody reaction is inhibited or not in the presence of the contaminant.

In the present invention, the test strip described above may be used as it is as an immunochromatographic device, or the test strip may be stored in a case to constitute an immunochromatographic device. In the former case, if a large volume of milk is used as a sample, the immunochromatographic device is preferably used by directly immersing one end of the test strip into the sample contained in a container. In the latter case, if the volume of milk as a sample is small, the immunochromatographic device is preferably used by measuring a predetermined volume of the sample with a pipette or the like, and dropping the sample to the test strip. In the latter case, the case may have any shape so long as the test strip can be stored. The case may be formed with any material, and preferred examples include polypropylene, polycarbonate, and so forth.

The immunochromatographic device of the present invention can also be provided as a kit comprising a container such as microtube, and an additive solution, for example, an additive solution containing a lytic enzyme or surfactant for lysing the bacterium to elute the ribosomal protein L7/L12 into the solution.

The immunochromatographic method of the present invention is an immunochromatographic method for detecting a specific substance contained in milk, which comprises: (1) the step of contacting the milk with a test strip having a first part retaining a labeled first antibody directed to the specific substance or retaining the specific substance that is labeled, a second part disposed downstream from the first part, on which a second antibody directed to the specific substance is immobilized, and a third part disposed upstream from the first part and the second part and having voids enabling removal of milk fat globules contained in the milk, at the third part or a further upstream part, and (2) the step of flowing the milk up to the second part or a further downstream part to obtain a detectable signal of the label at the second part or a further downstream part.

Milk is contacted with the aforementioned third part or a member for sample addition locating at a further upstream position, as it is, or as a mixed solution containing the additive solution. When the aforementioned specific substance is a substance existing in cells of a bacterium, the bacterium can be lysed by directly adding a surfactant ingredient to the milk, or the aforementioned additive solution, or making the surfactant ingredient to be retained in a part locating upstream from the aforementioned second part, preferably a part locating upstream from the aforementioned first part (as for the cell lysis treatment with a surfactant, refer to Japanese Patent Unexamined Publication (KOKAI) No. 61-111464). These techniques may be appropriately combined. As another component of the additive solution, an appropriate buffer (for example, MOPSO etc.) can be used, although the component is not particularly limited so long as a component that does not inhibit the antigen-antibody reaction is chosen.

As another embodiment, by directly adding a lytic enzyme to milk, or adding it to the additive solution, or immobilizing a lytic enzyme upstream from the aforementioned second part, preferably upstream from the aforementioned first part, milk subjected to the treatment with the lytic enzyme, in which the specific substance contained in the cells is exposed out of the cells, can be flown up to the second part or a further downstream part, and thus the specific substance existing in the cells of the bacterium can be detected at high sensitivity. These techniques may be appropriately combined. In a preferred embodiment, the lytic enzyme can be directly added to milk, or it can be contained in the aforementioned additive solution, and in a particularly preferred embodiment, the aforementioned additive solution containing a lytic enzyme can be added to milk.

Type of the lytic enzyme is not particularly limited, and two or more kinds of arbitrary lytic enzymes may also be used in combination. Since infections of *Escherichia coli*, bacteria belonging to the genus *Klebsiella*, and *Staphylococcus aureus* as etiologic bacteria of mastitis frequently occur, it is also preferable to use one or more kinds of lytic enzymes that can exhibit a bacteriolytic action against these microorganisms in combination. For example, one or two or more kinds of lytic enzymes selected from lysozyme, lysostaphin, pepsin, glucosidase, galactosidase, achromopeptidase, β-N-acetylglucosaminidase, and so forth can be used. For example, there has been proposed a method of using lysozyme and a cell membrane lytic agent as the lytic enzyme (Japanese Patent Unexamined Publication (KOKAI) No. 63-167799).

As the lytic enzyme, many of autolysins exhibit high lytic effect, and such autolysins are preferred (refer to FIG. 4). Autolysin refers to an enzyme that is produced by a bacterium itself, and lyses the bacterium itself. Although details of the reason why such autolysis occurs remain unknown, it is considered that, when a bacterium extends and divides, it plays a role of lysing and cleaving the bacterial cell. As bacterial autolysins, there are known lysostaphin, acetylglucosaminidase, achromopeptidase, and so forth.

When the presence of *Staphylococcus aureus* is especially suspected as an etiologic bacterium of mastitis, it may be preferable to use lysostaphin that specifically exhibits a bacteriolytic action against *Staphylococcus aureus* independently or in combination with another lytic enzyme, since lysis rate for *Staphylococcus aureus* exhibited by surfactants is low. Japanese Patent Unexamined Publication (KOKAI) No. 11-28099 discloses a method of lysing *Staphylococcus aureus* with lysostaphin, and those skilled in the art can easily obtain lysostaphin as a lytic enzyme. The entire disclosures of the aforementioned patent document are incorporated into the disclosures of the present specification by reference.

The naturally occurring type lysostaphin is a zinc protease produced by *Staphylocuccus simulans*, and it is known that it hydrolyzes glycylglycine bonds in the glycopeptide chains of the cell wall peptidoglycans of *Staphylococcus aureus* or congeneric bacterium thereof to lyse the bacterium. In this specification, the term lysostaphin also means, besides the naturally occurring type lysostaphin, a mutant lysostaphin having the amino acid sequence of the naturally occurring type lysostaphin, but including a mutation such as addition, deletion, and/or substitution of one or more amino acid residues in such a degree that the aforementioned hydrolysis activity is not lost. Further, the term lysostaphin also means a modified type lysostaphin consisting of the naturally occurring type lysostaphin or a mutant lysostaphin bound with another compound, for example, saccharide, polyethylene glycol, or the like. These lysostaphins can be obtained by the cultivation-based method or genetic engineering technique disclosed in Japanese Patent Unexamined Publication (KOKAI) No. 11-28099, or by purchasing a commercial product. When a lysostaphin is used as the lytic enzyme, for example, an antigen consisting of the ribosomal L7/L12 protein of *Staphylococcus aureus* can be detected by the immunochromatographic method, or such an antigen as mentioned above can also be detected with a combination of an immunochromatographic method and another immunological assay method, or another immunological assay method instead of the immunochromatographic method. Examples of the immunological assay method other than the immunochromatographic method include, for example, the agglutination reaction method, enzyme-linked immunosorbent assay (ELISA), radioimmunoassay (RIA), fluorescent immunoassay (FIA), and so forth, but it is not limited to these.

The antigen-antibody reaction can be detected by the sandwich assay method using the "labeled first antibody directed to the specific substance" retained by the first part, and the "second antibody directed to the specific substance" immobilized by the second part. Alternatively, the antigen-antibody reaction may be detected by the competitive assay method using the labeled specific substance retained by first part and the antibody directed to the specific substance immobilized on the second part. However, in the present invention, the sandwich assay method that provides high detection sensitivity and gives a line indicating detection of antibody as a positive result is preferred.

The immunochromatographic methods are roughly classified into those of the lateral flow type using transfer of a liquid by capillarity in a test strip disposed in the transverse direction, and those of the flow through type in which a liquid is passed through a vertically disposed test strip from the top to the bottom thereof mainly by gravity. Although both the lateral flow type and flow through type methods may be used in the present invention, the lateral flow type methods are more preferred.

The present invention will be further explained with reference to the following examples. However, the present invention is not limited by these examples.

EXAMPLES

Example 1: Confirmation of Liquid Flow of Milk Sample in Immunochromatographic Method (1) Preparation of Immunochromatographic Device The immunochromatographic device shown in FIG. 1 as a schematic sectional view was prepared as follows.

(a) Preparation of Ribosomal Protein L7/L12 Antibody

As the antibody to be labeled with gold colloid, *Staphylococcus aureus* ribosomal protein L7/L12 monoclonal antibody was used. According to the method described in International Patent Publication WO00/06603, Example 5, the *Staphylococcus aureus* L7/L12 ribosomal protein was obtained, and the monoclonal antibody was prepared by using this protein. As the monoclonal antibody, a combination of two kinds of monoclonal antibodies (SA-1 and SA-2) that can simultaneously bind to different sites of the aforementioned L7/L12 ribosomal protein.

It was confirmed that the combination of the monoclonal antibodies SA-1 and SA-2 react with the ribosomal protein L7/L12 of *Staphylococcus aureus*, but does not react with the ribosomal protein L7/L12 of bacteria that cause mastitis other than *Staphylococcus aureus*, and they are antibodies of which reactions are not inhibited by components of milk, as follows.

The monoclonal antibody SA-1 (10 µg/ml) and PBS (100 µl) were poured into each well of a 96-well ELISA plate (Maxsorp ELISA Plate, Nunc), and adsorption of the antibody was allowed overnight at 4° C. After the supernatant was removed, a 1% bovine serum albumin solution (in PBS, 200 µl) was added, and the reaction was allowed at room temperature for 1 hour to attain blocking. After the supernatant was removed, each well was washed several times with a washing solution (0.02% Tween 20, PBS), each of the various bacteria shown in Table 1 (about $1 \times 10^8$ cells/ml) diluted 10 times with 0.5% Triton X-100, PBS (100 µl) was added to the well, and the reaction was allowed at room temperature for 1 hour. Further, after the supernatant was removed, the monoclonal antibody SA-2 labeled with peroxidase and diluted with 0.02% Tween 20, PBS to a final concentration of 1 µg/ml (100 µl) was added, and the reaction was allowed at room temperature for 1 hour. After the supernatant was removed, each well was further washed several times with the washing solution, then a TMB solution (KPL, 100 µl) was added to each well, and the reaction was allowed at room temperature for 10 minutes. Then, 1 mol/l hydrochloric acid (100 µl) was added to terminate the reaction, absorbance was measured at 450 nm, and on the basis of the difference of the absorbance from the signal of the negative control (solution not containing bacterium), reactivity was evaluated. The results are shown in Table 1. The positive results (+) mean that the difference of the absorbance obtained after ELISA and the absorbance of the negative control was at least 0.5 or larger, and the negative results (−) mean that the difference of the absorbance obtained after ELISA and the absorbance of the negative control was not larger than 0.1.

TABLE 1

| Strain | Result |
|---|---|
| Bacillus subtilis | − |
| Chamydia pneumoniae | − |
| Enterrococcusfaecalis | − |
| Escherichia coli | − |
| Haemophilus influenzae | − |
| Haemophilus parahaemoliticus | − |
| Haemophilus parainfluenzae | − |
| Klebsiella pneumoniae | − |
| Legionella pneumophila | − |
| Moraxella catarrharis | − |
| Mycoplasma pneumoniae | − |
| Neisseria gonorrhoeae | − |
| Neisseria lactamica | − |
| Propionibacteriumacens | − |
| Proteus mirabilis | − |
| Pseudomonas aeruginosa | − |
| Serratiamarcescens | − |
| Staphylococcus aureus | + |
| Staphylococcus hominis | − |
| Staphylococcus chromogenes | − |
| Staphylococcus xylosus | − |
| Streptococcus agalactiae | − |
| Streptococcusintermedius | − |
| Streptococcus mitior | − |
| Streptococcus mitis | − |
| Streptococcus mutans | − |
| Streptococcus pneumoniae | − |
| Streptococcus pyogenes | − |
| Streptococcus salivarius | − |

The monoclonal antibody SA-1 (10 μg/ml) and PBS (100 μl) were poured into each well of a 96-well ELISA plate (Maxsorp ELISA Plate, Nunc), and adsorption of the antibody was allowed overnight at 4° C. After the supernatant was removed, a 1% bovine serum albumin solution (in PBS, 200 μl) was added, and the reaction was allowed at room temperature for 1 hour to attain blocking. After the supernatant was removed, each well was washed several times with a washing solution (0.02% Tween 20, PBS), Staphylococcus aureus (about 1×10$^8$ cells/ml) diluted 10 times with 0.5% Triton X-100, PBS (20 μl) and milk (commercial cow's milk to drink, 80 μl) were added to the well, and the reaction was allowed at room temperature for 1 hour. Further, after the supernatant was removed, the monoclonal antibody SA-2 labeled with peroxidase and diluted with 0.02% Tween 20, PBS to a final concentration of 1 μg/ml (100 μl) was added, and the reaction was allowed at room temperature for 1 hour. After the supernatant was removed, each well was further washed several times with the washing solution, then the TMB solution (KPL, 100 μl) was added, and the reaction was allowed at room temperature for 10 minutes. Then, 1 mol/l hydrochloric acid (100 μl) was added to terminate the reaction, then absorbance was measured at 450 nm, and on the basis of the difference of the absorbance from the signal of the positive control (solution not containing milk), reactivity was evaluated to confirm that the reactivity was not reduced by milk.

(b) Gold Colloid-labeled Antibody-impregnated Member

A gold colloid solution (particle size 60 nm, 0.9 mL, BB International) was mixed with 0.1 M potassium phosphate, pH 7.5, the monoclonal antibody SA-2 to be labeled with gold colloid (100 μg/mL) was added to the mixture, and the mixture was left standing at room temperature for 5 minutes so that the antibody bound to the gold colloid particle surfaces. Then, a 10% aqueous solution of bovine serum albumin (BSA) was added at a final concentration of 1% in the gold colloid solution, and the remaining surfaces of the gold colloid particles were blocked with BSA to prepare a solution of the monoclonal antibody SA-2 labeled with gold colloid (henceforth referred to as "gold colloid-labeled antibody"). This solution was centrifuged (at 15000× rpm for 5 minutes) to precipitate the gold colloid-labeled antibody, and the supernatant was removed to obtain the gold colloid-labeled antibody. This gold colloid-labeled antibody was suspended in 20 mM Tris-hydrochloric acid buffer (pH 8.2) containing 0.25% BSA, 2.5% sucrose, and 35 mM NaCl to obtain a gold colloid-labeled antibody solution. A glass fiber pad of a strip-like shape (10 mm×300 mm) was impregnated with the gold colloid-labeled antibody solution (2 mL), and dried at room temperature under reduced pressure to obtain a gold colloid-labeled antibody-impregnated member 1 (first part).

(c) Part for Capturing Complex of Antigen and Gold Colloid-labeled Antibody

A nitrocellulose membrane having a width of 25 mm and a length of 300 mm was prepared as a membrane carrier 2 for chromatographic development with chromatography medium (second part).

A solution containing the monoclonal antibody SA-1 (1.5 mg/mL) was applied in the shape of a line in a volume of 1 μL/cm to the membrane carrier 2 for chromatographic development at a position of 10 mm from the end on the side of the chromatography development starting point, and dried at 50° C. for 30 minutes, and then the membrane carrier was immersed in a 0.5% sucrose solution for 30 minutes, and dried overnight at room temperature to obtain a part 3 for capturing the complex of the Staphylococcus aureus ribosomal protein L7/L12 antigen and the gold colloid-labeled antibody.

(d) Preparation of Immunochromatographic Device

In addition to the aforementioned labeled antibody-impregnated member 1 and membrane carrier 2 for chromatographic development, cotton cloth serving as the member 4 for sample addition and the member 7 for removal of fat globules (third part), and filter paper as the member 5 for absorption were prepared. After these members were adhered on the substrate 6 (thickness 254 μm, made of polystyrene, having adhesive for adhering members), the substrate was cut in a width of 5 mm to prepare the immunochromatographic device of which sectional view is shown in FIG. 1. As the member 4 for sample addition, the members shown in Table 2 were used.

TABLE 2

| Member for sample addition (manufacturer) | Retention particle size (μm) | Material | Thickness (μm) |
|---|---|---|---|
| GF/B (GE Healthcare Bioscience) | 1.0 | Glass fiber | 980 |
| GF/AVA (GE Healthcare Bioscience) | 1.7 | Glass fiber | 299 |
| MF1 (GE Healthcare Bioscience) | 2 | Glass fiber | 357 |
| VF1 (GE Healthcare Bioscience) | 2.5 | Glass fiber | 701 |
| VF2 (GE Healthcare Bioscience) | 3 | Glass fiber | 764 |
| GF/DVA (GE Healthcare Bioscience) | 3.5 | Glass fiber | 776 |
| NE107 (Asahi Kasei Fibers) | Several 10s to several 100s | Cellulose | 410 |
| UR601 (Asahi Kasei Fibers) | Several 10s to several 100s | Cellulose | 520 |

(2) Test

Measurement for cow's milk using the immunochromatographic device was performed as follows. A fresh milk sample (100 μl) from which Staphylococcus aureus was detected was put into a microtube, an additive solution (150 μl, 1% Tween 20, 0.05 M NaCl, 0.1 M MOPSO as final concentrations, pH 7.5) was added to the sample and mixed. The immunochromatographic device obtained in (1) mentioned above was immersed into the above mixed solution from the member 4 for sample addition, chromatographic development was carried out by the lateral flow method, and it was examined whether the developing solution would flow to the member 5 for absorption.

The results are shown in Table 3. The symbol + indicates that the developing solution flowed to the member 5 for absorption, and the symbol − indicates that the developing solution stopped on the way to the member 5 for absorption. Only when a member showing a retention particle size not larger than 3.5 μm was used, the solution flowed to the member 5 for absorption. In the other cases, the liquid flow stopped in the middle of the membrane carrier 2 for chromatographic development.

TABLE 3

| Member for sample addition (manufacturer) | Result |
|---|---|
| GF/B (GE Healthcare Bioscience) | + |
| GF/AVA (GE Healthcare Bioscience) | + |
| MF1 (GE Healthcare Bioscience) | + |
| VF1 (GE Healthcare Bioscience) | + |
| VF2 (GE Healthcare Bioscience) | + |
| GF/DVA (GE Healthcare Bioscience) | + |
| NE107 (Asahi Kasei Fibers) | − |
| UR601 (Asahi Kasei Fibers) | − |

Example 2: Detection of *Staphylococcus aureus* in Milk by Immunochromatographic Method (1) Preparation of Immunochromatographic Device According to the method described in Example 1, the immunochromatographic device shown in FIG. 1 was prepared. As the member serving as the member 4 for sample addition and the member 7 for removal of fat globules (third part), GF/DVA mentioned in Table 2 was used.

(2) Test

Measurement for cow's milk using the immunochromatographic device was performed as follows. Each of fresh milk samples 1 to 6 (100 μl) was put into a microtube, an additive solution (150 μl, 1% Tween 20, 0.05 M NaCl, 0.1 M MOPSO as final concentrations, pH 7.5) was added to the sample and mixed. The aforementioned immunochromatographic device was immersed into the above mixed solution from the member 4 for sample addition, the device was left standing at room temperature for 15 minutes to carry out chromatographic development by the lateral flow method, and then whether the complex of the ribosomal protein L7/L12 antigen and the gold colloid-labeled antibody was captured by the aforementioned part 3 for capturing or not was visually determined on the basis of the presence or absence of a reddish purple line that became more or less conspicuous in proportion to the capture amount.

Separately, in order to confirm the presence or absence of *Staphylococcus aureus* in the milk samples, detection was also performed by the cultivation-based method. Each milk sample (100 μl) was inoculated to Trypticase Soy Agar II with 5% Sheep Blood (Becton Dickinson Japan) or the *Staphylococcus aureus* selection medium, X-SA Agar Medium (Nissui), then incubation was performed at 37° C. for 24 hours, and the colonies appeared were confirmed.

The results of the visual determination and the results of the cultivation-based method are shown in Table 4. In the results of the cultivation-based method, the symbol + indicates that a colony of *Staphylococcus aureus* was observed, and the symbol − indicates that colony of *Staphylococcus aureus* was not observed. In the results obtained by determination using the kit, the symbol + indicates that a reddish purple line could be visually observed, and the symbol − indicates that such a line could not be visually observed.

TABLE 4

| Sample No. | Results obtained by cultivation-based method (detected bacterium) | Results obtained by determination with kit |
|---|---|---|
| 1 | − | − |
| 2 | − | − |
| 3 | − (*Streptococcus*) | − |
| 4 | − (*Streptococcus*) | − |
| 5 | + (*Staphylococcus aureus*) | + |
| 6 | + (*Staphylococcus aureus*) | + |

For the two milk samples for which no bacteria were detected, any line did not appear. Also for the two samples for which *streptococcus* was detected, any line did not appear. On the other hand, for the samples for which *Staphylococcus aureus* was detected, lines appeared, and thus *Staphylococcus aureus* could be detected.

As described above, use of the immunochromatographic device of the present invention made it possible to develop a milk sample containing milk fat globules without clogging in membrane, and perform accurate measurement.

Example 3: Measurement with Milk at High Concentration by Immunochromatographic Method The immunochromatographic device shown in FIG. 1 was prepared by the method described in Example 1, and liquid flow was confirmed with changing ratio of milk in samples. As the member for sample addition, those mentioned in Table 3 were used. A fresh milk sample and an additive solution were mixed at various ratios (additive solution contained 1% Tween 20, 0.05 M NaCl, 0.1 M MOPSO as final concentrations, pH 7.5, total liquid volume was 250 μl), the immunochromatographic device was immersed into the mixture from the member for sample addition, chromatographic development was carried out by the lateral flow method, and whether the total volume of the mixture was developed or not was examined.

The results are shown in Table 5. The symbol + indicates that the developing solution flowed to the member 5 for absorption, and the symbol − indicates that the developing solution stopped on the way to the member 5 for absorption. When the ratio of milk was 50%, the total volume of the mixture flowed to the member 5 for absorption with the members for sample addition other than VF1. When the ratio of milk was 70%, for all of the members for sample addition, the flow of the mixture stopped in the middle of the membrane carrier 2 for chromatographic development, or even if the mixture reached the member 5 for absorption, flow of the mixture stopped, and thus correct measurement could not be performed, as a result.

TABLE 5

| Member for sample addition | Result (ratio of milk, %) | |
|---|---|---|
| (manufacturer) | 50 | 70 |
| GF/AVA (GE Healthcare Bioscience) | + | − |
| MF1 (GE Healthcare Bioscience) | + | − |
| VF1 (GE Healthcare Bioscience) | − | − |
| VF2 (GE Healthcare Bioscience) | + | − |
| GF/DVA (GE Healthcare Bioscience) | + | − |

Then, two of the members for sample addition were stacked, and used to perform the same test as mentioned above. Two of the members for sample addition were stacked as shown in FIG. 3. As the members for sample addition, GF/AVA and GF/DVA were used. GF/DVA was disposed on the upstream side (member 4 for sample addition), and GF/AVA was disposed on the downstream side (member 7 for removal of fat globules), and the test was performed with various lengths of the members. The milk ratio was 80%, and the volume of the sample was 250 μl. The results are shown in Table 6 (as for "Length" and "Overlap" mentioned in the table, refer to FIG. 3). The symbol + indicate that the developing solution flowed to the member 5 for absorption. Even when the milk rate was 80%, the liquid flow did not stop, and correct measurement could be performed. Furthermore, even when the lengths of two of the members for sample addition were changed, correct measurement could be performed.

TABLE 6

| Member for sample addition | | Overlap | |
|---|---|---|---|
| Length (mm) | | | |
| GF/DVA | GF/AVA | (mm) | Test result |
| 25 | 10 | 5 | + |
| 20 | 15 | 5 | + |
| 15 | 20 | 5 | + |
| 10 | 25 | 5 | + |
| 30 | 25 | 25 | + |
| 21 | 25 | 16 | + |
| 16 | 25 | 11 | + |
| 25 | 10 | 5 | + |
| 25 | 15 | 10 | + |
| 25 | 20 | 15 | + |

As described above, by using two kinds of the members for sample addition having different retention particle sizes in combination, milk fat globules could be removed, the milk samples could be developed without clogging in the membrane, and thus highly sensitive and correct measurement was enabled, even when milk was used at high concentration.

Example 4: Effect of Lytic Enzyme in Detection of *Staphylococcus aureus* by Enzyme-linked Immunosorbent Assay (ELISA)

(a) Preparation of Monoclonal Antibody Against Ribosomal Protein L7/L12

The monoclonal antibodies SA-1 and SA-2 mentioned in Example 1 were used.

(b) Confirmation of Effect of Lytic Enzyme in ELISA

The effect of lytic enzyme was confirmed as follows.

*Staphylococcus aureus* was treated with each of the surfactant and lytic enzymes shown in Table 7 at 37° C. for 20 minutes in 10 mM Tris-HCl (pH 8.0), and then used for ELISA, in which absorbance was measured in the same manner as that of Example 1, (a). *Staphylococcus aureus* was adjusted to a final concentration of $2.5 \times 10^5$ (cells/ml) with physiological saline. As the negative control, phosphate buffered saline (PBS) was used. For the positive control, a nonionic surfactant, Triton X-100, was used. The final concentration was 1%, and the treatment was performed overnight at room temperature.

TABLE 7

| Surfactant or lytic enzyme | Type | Manufacturer | Concentration (final concentration) |
|---|---|---|---|
| PBS | Buffer | Wako Pure Chemical Industries | — |
| Triton X-100 | Surfactant | SIGMA | 1.0% |
| Lysozyme | Lytic enzyme | Wako Pure Chemical Industries | 5 (μg/ml) |
| Achromopeptidase | Lytic enzyme | Wako Pure Chemical Industries | 5 (μg/ml) |
| Lysostaphin | Lytic enzyme | Wako Pure Chemical Industries | 5 (μg/ml) |

The results are shown in FIG. 4.

Compared with PBS used as the negative control, higher absorbance was obtained with the surfactant and all of the lytic enzymes. Compared with the surfactant Triton X-100, which is a commonly used lysing agent, achromopeptidase and lysostaphin, which are autolysins, gave twice higher absorbance vales.

Example 5: Effect of Lytic Enzyme in Case of Using Milk

By using achromopeptidase (Wako Pure Chemical Industries) and lysostaphin (Wako Pure Chemical Industries), which showed high lysing effect in Example 4, *Staphylococcus aureus* added to cow's milk was measured by ELISA. As the cow's milk, commercial cow's milk to drink was used at a ratio of 0 to 80% (remainder was 10 mM Tris-HCl (pH 8.0)), and *Staphylococcus aureus* was adjusted to a final concentration of $1 \times 10^5$ (cells/ml) with physiological saline. Concentrations of achromopeptidase and lysostaphin were adjusted by using 10 mM Tris-HCl (pH 8.0), and they were mixed with *Staphylococcus aureus* samples at a final concentration of 5 μg/ml. The measurement by ELISA was performed in the same manner as that of Example 4.

The results are shown in FIG. 5. When achromopeptidase was used, the absorbance decreased with increase of the ratio of milk. On the other hand, when lysostaphin was used, regardless of the ratio of milk, a fixed absorbance was observed. Thus, the results indicate that achromopeptidase cannot exhibit sufficient effect in the presence of milk of high concentration.

Example 6: Detection of *Staphylococcus aureus* in Milk by Immunochromatographic Method (1) Preparation of Immunochromatographic Device An immunochromatographic device was prepared as follows.

(a) Gold Colloid-labeled Antibody-impregnated Member

The gold colloid-labeled antibody-impregnated member described in Example 1 was used.

(b) Part for Capturing Complex of Antigen and Gold Colloid-labeled Antibody

This part was prepared in the same manner as that of Example 1.

(c) Preparation of Immunochromatographic Device

In addition to the aforementioned labeled antibody-impregnated member 1 and membrane carrier 2 for chromatographic development, GF/DVA (filter member consisting of glass fibers having a thickness of 776 μm, and a retention particle size of 3.5 μm, GE Healthcare Bioscience) as a member serving as both the member 4 for sample addition and the member 7 for removal of fat globules (third part), and filter paper as the member 5 for absorption were prepared. After these members were adhered on the substrate 6 (thickness 254 μm, made of polystyrene, having adhesive for adhering members), the substrate was cut in a width of 5 mm to prepare the immunochromatographic device of which sectional view is shown in FIG. 6.

(2) Test

Measurement for cow's milk using the immunochromatographic device was performed as follows.

A milk sample (100 μl) containing a known amount of Staphylococcus aureus was put into a microtube, an additive solution (150 μl, 1% Triton X-100, 5 μg/ml of lysostaphin, 0.1 M MOPSO as final concentrations, pH 7.5) was added to the sample and mixed. As the milk, commercial product to drink was used. For comparison, the test was also performed with the additive solution not containing lysostaphin (1% Triton X-100, 0.1 M MOPSO as final concentrations, pH 7.5). The aforementioned immunochromatographic device was immersed into the above mixed solution from the member 4 for sample addition, the device was left standing at room temperature for 30 minutes to carry out chromatographic development by the lateral flow method, and then whether the complex of the ribosomal protein L7/L12 antigen and the gold colloid-labeled antibody was captured by the aforementioned part 3 for capturing or not was determined by quantifying a reddish purple line, which became more or less conspicuous in proportion to the capture amount, using an apparatus, FASTKIT Immunochromatographic Reader DiaScan 20-A (Becton Dickinson Japan).

The results are shown in FIG. 7. When the additive solution containing lysostaphin was used, it was found that the curve shifted to the low concentration side from the position of the curve obtained with the additive solution containing Triton X-100 instead of lysostaphin, as a result, and Staphylococcus aureus can be detected with about 10 times higher sensitivity.

Example 7: Measurement for Milk Sample by Immunochromatographic Method

An immunochromatographic device was prepared in the same manner as that of Example 6.

A fresh milk sample (100 μl) from which Staphylococcus aureus was detected was put into a microtube, an additive solution (150 μl) was added to the sample, and mixed at room temperature. As the additive solution, two kinds of the additive solutions described in Example 6 were used. The measurement was performed in the same manner as that of Example 6, and then a reddish purple line appeared was visually evaluated (positive +, negative −).

On the other hand, in order to confirm the number of Staphylococcus aureus in the milk samples, quantification was performed by the cultivation-based method. Each milk sample (100 μl) was inoculated to Trypticase Soy Agar II with 5% Sheep Blood (Becton Dickinson Japan) or the Staphylococcus aureus selection medium, X-SA Agar Medium (Nissui), then incubation was performed at 37° C. for 24 hours, and the colonies appeared were counted.

The number of Staphylococcus aureus counted by the cultivation-based method and the determination results obtained by the immunochromatographic method are shown in Table 8. When lysostaphin was not added, $1 \times 10^4$ (cfu/ml) or fewer Staphylococcus aureus could not be detected, but when lysostaphin was added, it became possible to detect up to $5 \times 10^3$ of Staphylococcus aureus.

TABLE 8

| Sample No. | Number of Staphylococcus aureus (cfu/ml) | Results of measurement with kit | |
|---|---|---|---|
| | | With lysostaphin | Without lysostaphin |
| 1 | $5 \times 10^3$ | + | − |
| 2 | $1 \times 10^4$ | + | − |
| 3 | $1 \times 10^4$ | + | − |
| 4 | $1 \times 10^4$ | + | − |
| 5 | $1 \times 10^4$ | + | − |
| 6 | $1 \times 10^5$ | + | + |

INDUSTRIAL APPLICABILITY

The present invention can be used for diagnosis of infectious diseases of livestock animals.

The invention claimed is:

1. A detection kit comprising
   an additive solution comprising a lytic enzyme or a surfactant, and
   an immunochromatographic device, wherein the device comprises a test strip having:
   a first part retaining a labeled first antibody directed to a specific substance or retaining the specific substance that is labeled,
   a second part disposed downstream from the first part, on which a second antibody directed to the specific substance is immobilized, and
   a third part disposed upstream from the second part and having voids enabling removal of milk fat globules contained in milk, wherein the third part is constituted by a first member disposed downstream and a second member disposed upstream, and retention particle size of the voids of the first member is 1.0 to 2.0 μm, and retention particle size of the voids of the second member is 3.0 to 3.5 μm,
   wherein the specific substance is in a bacterium causative of mastitis, wherein the additive solution can lyse the bacterium in milk to release the specific substance from the bacterium, and wherein a label of the labeled first antibody or of the specific substance that is labeled is capable of passing through the voids of the test strip.

2. The kit of claim 1, wherein the label comprises a coloring particle.

3. The kit of claim 1, wherein the coloring particle has a size of 10 to 100 nm in diameter.

4. The kit of claim 1, wherein the bacterium is Escherichia coli or Staphylococcus aureus.

5. The kit of claim 1, wherein the additive solution comprises achromopeptidase or lysostaphin.

* * * * *